US010782211B2

United States Patent
Zhang et al.

(10) Patent No.: US 10,782,211 B2
(45) Date of Patent: Sep. 22, 2020

(54) GATHERING AND SAMPLING DEVICE AND INSPECTION APPARATUS

(71) Applicants: Tsinghua University, Beijing (CN); Nuctech Company Limited, Beijing (CN)

(72) Inventors: Qingjun Zhang, Beijing (CN); Yuanjing Li, Beijing (CN); Ziran Zhao, Beijing (CN); Ge Li, Beijing (CN); Biao Cao, Beijing (CN); Qiufeng Ma, Beijing (CN); Linxia Tan, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 119 days.

(21) Appl. No.: 15/858,829

(22) Filed: Dec. 29, 2017

(65) Prior Publication Data

US 2018/0188138 A1 Jul. 5, 2018

(30) Foreign Application Priority Data

Dec. 29, 2016 (CN) .......................... 2016 1 1255800

(51) Int. Cl.
*G01N 1/22* (2006.01)
*G01N 1/02* (2006.01)
(Continued)

(52) U.S. Cl.
CPC ............. *G01N 1/2205* (2013.01); *G01N 1/02* (2013.01); *G01N 1/22* (2013.01); *G01N 1/44* (2013.01);
(Continued)

(58) Field of Classification Search
CPC .. G01N 1/2205; G01N 1/02; G01N 2001/028; G01N 2001/022; G01N 33/0057; G01N 1/22; G01N 1/44
(Continued)

(56) References Cited

U.S. PATENT DOCUMENTS

| 8,963,076 B2 * | 2/2015 | Jong ...................... G01N 35/10 250/281 |
| 2003/0155506 A1 | 8/2003 | Motchkine et al. |

(Continued)

FOREIGN PATENT DOCUMENTS

JP 2014-174074 A 9/2014

OTHER PUBLICATIONS

Office Action dated Nov. 26, 2018 for Japanese Patent Application No. 2018-000087, which corresponds in priority to the above-identified subject U.S. application.

*Primary Examiner* — Marrit Eyassu
(74) *Attorney, Agent, or Firm* — Knobbe, Martens, Olson & Bear, LLP

(57) ABSTRACT

A sampling device and an inspection apparatus are disclosed. In one aspect, an example gathering and sampling device includes a cylindrical outer housing and an inner housing disposed within the cylindrical outer housing, a cyclone chamber is formed between the cylindrical outer housing and the inner housing to generate a cyclone by injecting a gas flow into the cyclone chamber. The gathering and sampling device further includes an outer chamber body, and a plurality of gas injection orifices formed in the first inner housing end opening of the inner housing and configured to inject a gas towards a substantial center of a circular region defined by an end face of the first outer housing end opening of the cylindrical outer housing.

14 Claims, 1 Drawing Sheet

(51) Int. Cl.
*G01N 1/44* (2006.01)
*G01N 33/00* (2006.01)

(52) U.S. Cl.
CPC ... *G01N 33/0057* (2013.01); *G01N 2001/022* (2013.01); *G01N 2001/028* (2013.01)

(58) Field of Classification Search
USPC ..................................................... 73/863.23
See application file for complete search history.

(56) References Cited

U.S. PATENT DOCUMENTS

| | | | |
|---|---|---|---|
| 2004/0227073 A1* | 11/2004 | Krasnobaev | G01N 27/622 250/288 |
| 2005/0054506 A1* | 3/2005 | Bradley | B01L 3/5021 494/31 |
| 2007/0158447 A1 | 7/2007 | Bunker | |
| 2008/0314166 A1 | 12/2008 | Settles | |
| 2009/0050801 A1* | 2/2009 | Fedorov | H01J 49/066 250/288 |
| 2011/0159596 A1* | 6/2011 | Keinan | G01N 1/2211 436/52 |
| 2011/0203931 A1 | 8/2011 | Novosselov et al. | |
| 2014/0151543 A1* | 6/2014 | Nagano | G01N 1/2214 250/282 |

\* cited by examiner

GATHERING AND SAMPLING DEVICE AND INSPECTION APPARATUS

CROSS-REFERENCE TO RELATED APPLICATION

The present application claims priority to Chinese Patent Application No. 201611255800.3, filed on Dec. 29, 2016, entitled "GATHERING AND SAMPLING DEVICE AND INSPECTION APPARATUS", which is incorporated herein by reference in its entirety.

BACKGROUND OF THE DISCLOSED TECHNOLOGY

Field of the Technology

The disclosed technology relates to the field of inspection system, and particularly, to a collecting and sampling device.

Description of the Related Technology

In order to prevent terrorist activities and drug smuggling, many explosive and drug detection technologies have been and are undergoing development. To promote and prompt detection at transit points, a fast and efficient sampling device for trace substances is required. In particular interest here, it is desired to provide a high efficiency sampling device having wider selectivity on boiling points ranges of substances.

SUMMARY OF CERTAIN INVENTIVE ASPECTS

An object of certain aspects of the disclosed technology is to provide a gathering and sampling device, including:

a cylindrical outer housing including a first outer housing end opening;

an inner housing disposed within the cylindrical outer housing and including a first inner housing end opening, a cyclone chamber being formed between the cylindrical outer housing and the inner housing to generate a cyclone by injecting a gas flow into the cyclone chamber;

an outer chamber body a portion of an end of the outer chamber body being the inner housing, and a plurality of gas injection orifices formed in the first inner housing end opening of the inner housing and configured to inject a gas towards a substantial center of a circular region defined by an end face of the first outer housing end opening of the cylindrical outer housing.

In one embodiment, low circumference portion of the outer housing is sleeved on upper outer circumference portion of the outer chamber body and the inner housing seats on upper circumference portion of the outer chamber body.

In one embodiment, the outer chamber body further includes a gas guiding chamber formed by inner space of the outer chamber body, and a sampling opening located at a center of the inner housing and configured to guide a gas sample, that is adsorbed to the gathering and sampling device through a center of the cyclone, into the gas guiding chamber.

In one embodiment, the outer chamber body further includes a gas charging chamber formed in a side wall of the outer chamber body around the gas guiding chamber and a plurality of rotational flow tubes connected with the gas charging chamber and injecting the gas from the gas charging chamber into the cyclone chamber so as to generate the cyclone by injecting the gas flow into the cyclone chamber.

In one embodiment, the plurality of gas injection orifices are communicated with the gas charging chamber, and the plurality of gas injection orifices have a gas-flow rate smaller than that from the plurality of rotational flow tubes.

In one embodiment, the gas guiding chamber is provided therein with an inner gas guiding cylinder defining an inner gas guiding chamber, a gas guided in from the sampling opening enters about a bottom of the inner gas guiding chamber and then flows out of the inner gas guiding chamber through an inner gas guiding chamber opening.

In one embodiment, the inner gas guiding cylinder is configured to heat so as to increase a temperature of the gas entering the inner gas guiding cylinder.

In one embodiment, an outer wall of the inner gas guiding cylinder and an inner wall of the gas guiding chamber define an outer gas guiding chamber, a thermal desorption room defined by a filtering screen is formed within the outer gas guiding chamber, and in the thermal desorption room the sample is extracted through a semi-permeable membrane disposed in the thermal desorption room.

In one embodiment, the semi-permeable membrane defines a desorption space, the sample in the outer gas guiding chamber can pass through the semi-permeable membrane and enter the desorption space, and the gathering and sampling device further includes a carrier gas tube and a sample outlet, and a carrier gas is introduced by the sample carrier tube and is mixed with the desorbed sample and then is discharged at the sample outlet;

wherein, the semi-permeable membrane is configured to be supported by a support screen, to form the cylindrical structure of multiple-layered semi-permeable membranes or the grid structure of a multiple-layered semi-permeable membrane, so as to facilitate the gas mixed with the sample to contact the semi-permeable membrane.

In one embodiment, the outer housing has a trumpet shape.

In one embodiment, the plurality of rotational flow tubes are provided uniformly in a circumferential wall of the outer chamber body closing to the first inner housing end opening, and axes of the rotational flow tubes are tangent with side wall of the outer chamber body, and angles of the axes of the rotational flow tubes relative to a vertical direction are between 45°~90°.

In one embodiment, the outer housing is formed with at least one gas inlet located at a lower part of the side wall of the outer housing, and at an opposite side of the first outer housing end opening relative to the rotational flow tubes, such that the gas is absorbed through the at least one gas inlet under the action of the cyclone generated in the cyclone chamber.

In one embodiment, an exhaust tube is provided at a lower part of the side wall of the gas charging chamber, and the gas in the outer gas guiding chamber is discharged through the exhaust tube and is re-sent by a pump to the gas charging chamber for recycling.

In one embodiment, the outer chamber body is surrounded by a thermal insulation layer, and a heater is provided in the outer chamber body for controlling the outer chamber body to be in a desired temperature.

According to another aspect of the disclosed technology, there is provided an inspection apparatus including the abovementioned gathering and sampling device.

DETAILED DESCRIPTION OF CERTAIN ILLUSTRATIVE EMBODIMENTS

Although the disclosed technology allows various modifications and alternatives, specific embodiments of the disclosed technology will be shown in the attached drawings and will be described in detail herein. However, it should be understood that, the attached drawings and the detailed description are not be construed as limiting the disclosed technology to the specific forms disclosed herein, but in contrary, intends to cover all of changes, equivalent alternatives, replacements, made within principles and spirit of the disclosed technology, and the scope of which is defined in the claims. The drawings are provided schematically and thus are not drawn in scales.

Several embodiments of the disclosed technology will be further described hereinafter with reference to the attached drawings.

Figure 1:
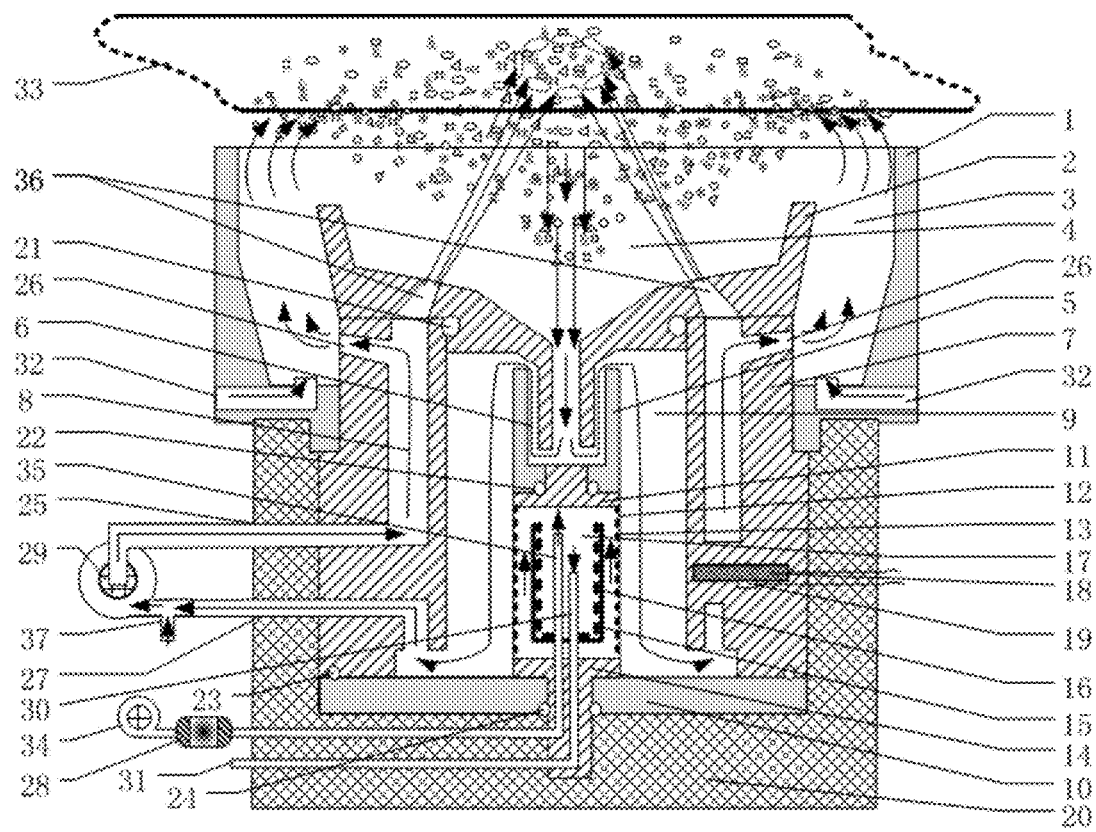
FIG. 1 is a schematic sectional view of a gathering and sampling device according to an embodiment of the disclosed technology.

According to one embodiment of the disclosed technology, there is provided a gathering and sampling device, including an outer housing, such as cylindrical outer housing 1 (e.g., cylindrically outer housing). The cylindrical outer housing 1 includes a first outer housing end opening, for example, an upper opening of the outer housing 1 as shown in FIG. 1. An inner housing 2 is disposed within the cylindrical outer housing 1 and includes a first inner housing end opening, as shown in FIG. 1. It is shown in FIG. 1 that the first outer housing end opening is greater in height than the first inner housing end opening. However, it should be noted that, the first outer housing end opening may be flush with the first inner housing end opening, or may be substantially at a similar level. Herein, it should be noted that, terms "upper", "lower", "in height" are used according to orientations in FIG. 1 for the description. Obviously, the device in FIG. 1 may be disposed transversely or with its opening downwards. In addition, in FIG. 1, the outer housing 1 may have a trumpet shape, alternatively, the outer housing 1 may have a cylindrical shape.

A cyclone chamber 3 is formed between the cylindrical outer housing 1 and the inner housing 2 so as to generate a cyclone by injecting a gas flow into the cyclone chamber 3. The gathering and sampling device further includes an outer chamber body 7, a portion of an end of the outer chamber body being the inner housing 2, and a plurality of gas injection orifices 36 formed in the first inner housing end opening of the inner housing 2 and configured to inject a gas towards a substantial center of a circular region defined by an end face of the first outer housing end opening of the cylindrical outer housing 1.

In this embodiment, the outer housing 1 is formed with at least one gas inlet 32 located, as shown in FIG. 1, at a lower part of the side wall of the outer housing 1 and at an opposite side of the first outer housing end opening relative to the rotational flow tubes 26, such that the gas is absorbed through the at least one gas inlet under the action of the cyclone generated in the cyclone chamber 3. Since a tornado cyclone is formed within the cyclone chamber 3 and the cyclone generates an adsorption effect, external gas is absorbed into the tornado cyclone through the gas inlet 32 provided as shown in FIG. 1, which facilitates on formation and amplification of the tornado cyclone. The number of the gas inlets 32 may be determined according to size of the cyclone chamber, for example, may be six, seven, eight, nine, ten or more, and they are distributed discretely at the lower part of side wall of the outer housing 1, however, preferably, the plurality of gas inlet 32 are distributed at uniform internal at the lower part of side wall of the outer housing 1.

Negative pressure center of the tornado cyclone generated in the cyclone generating part according to the present embodiment has strong absorption force on sample, and thus has efficient absorption on particle samples.

In one embodiment, the outer chamber body 7 further includes a gas guiding chamber formed by inner space of the outer chamber body 7, and a sampling opening 4 located at a center of the inner housing 2. In other words, the outer chamber body 7 defines therein a gas guiding chamber. The sampling opening 4 is configured to guide a gas sample, that is adsorbed to the gathering and sampling device through a center of the tornado cyclone, into the gas guiding chamber. When the gathering and sampling device faces the sample, after the tornado cyclone is generated, a gas absorption effect in an opposing direction is created in the center of the tornado cyclone. In FIG. 1, a downward gas flow is created in the center of the tornado cyclone, thus the sample is absorbed into the gas guiding chamber by the downward gas flow. In this embodiment, a plurality of gas injection orifices 36 are provided to inject a gas flow towards a position of the sample in the center of the cyclone, which blows the sample on an object to be inspected out of or apart from the object to be inspected, after that, the sample, together with the downward gas flow, is adsorbed into the gas guiding chamber. Provision of the plurality of gas injection orifices 36 can improve an impact force of the gas flow on the object to be inspected so as to crash down high boiling point particle samples, thereby improving efficiency of sample collection and widening the range of the sample which can be collected by the gathering and sampling device according to the present embodiment. It should be noted that, the number of the gas injection orifices 36 may be determined according to size of the outer chamber body 7, for example, may be four, five, six, seven, eight, ten or more, and they are distributed discretely at the upper part of the outer chamber body 7, however, preferably, the plurality of gas injection orifices 3 are distributed at uniform internal at the upper part of the outer chamber body 7.

According to embodiments of the disclosed technology, the outer chamber body 7 further includes a gas charging chamber 8 formed in a side wall of the outer chamber body 7 around the gas guiding chamber and a plurality of rotational flow tubes 26 connected with the gas charging chamber 8. The rotational flow tubes 26 inject gas from the gas charging chamber 8 into the cyclone chamber 3 so as to generate the cyclone by forming the gas flow within the cyclone chamber 3. According to the present embodiment, the plurality of rotational flow tubes 26 are provided uniformly in a circumferential wall of the outer chamber body 7 closing to the first inner housing end opening, and axes of the rotational flow tubes 26 are tangent with side wall of the outer chamber body 7, and angles of the axes of the rotational flow tubes 26 relative to a vertical direction are between 45°~90°. Due to the manner of arrangement of the rotational flow tubes 26, the gas injected from the rotational flow tubes 26 form a cyclone in the cyclone chamber 3. The number of the rotational flow tubes 26 may be determined according to size of the outer chamber body 7, for example, may be four, five, six, seven, eight, ten or more, and they are distributed discretely at the upper part of the outer chamber body 7, however, preferably, the plurality of rotational flow tubes 26 are distributed at uniform internal at the upper part of the outer chamber body 7.

In the present embodiment, the plurality of gas injection orifices 36 are communicated with the gas charging chamber 8. And, a gas-flow rate discharged from the plurality of gas injection orifices 36 is smaller than that from the plurality of rotational flow tubes 26. This can be achieved by designing aperture sizes of the gas injection orifices 36 and the rotational flow tubes 26. For example, aperture size of the rotational flow tubes 26 is five to ten times the size of the gas injection orifices 36. However, it should be noted that, other sizes of them can be adopted.

In the present embodiment, the gas guiding chamber is provided therein with an inner gas guiding cylinder 5 defining an inner gas guiding chamber 6. A gas guided in from the sampling opening 4 enters about a bottom of the inner gas guiding chamber 6 and then flows out of the inner gas guiding chamber through an inner gas guiding chamber opening. As shown in FIG. 1, through the sampling opening 4, the gas mixed with the collected sample is guided into the bottom of the inner gas guiding chamber 5, by this way, the gas stays in the inner gas guiding cylinder 5 for increased time, which helps heating the gas in the inner gas guiding cylinder 5, lengthens a distance in which the collected sample is desorbed and dispersed, thereby sufficiently dispersing into single molecules. Here, the inner gas guiding cylinder 5 can be configured to heat so as to increase a temperature of the gas entering the inner gas guiding cylinder 5. The gas can enter the sampler freely after the gas is dispersed into molecules in the inner gas guiding cylinder 5. The inner gas guiding chamber 6 is designed to lengthen the length in which the collected sample is desorbed and dispersed and to sufficiently disperse the particles and clusters of the sample into single molecules, thereby not only reducing inspection limit to high boiling point, but also improving the resolution.

In the present embodiment, an outer wall of the inner gas guiding cylinder 5 and an inner wall of the gas guiding chamber 6 define an outer gas guiding chamber 9, a thermal desorption room 17 defined by a filtering screen is formed within the outer gas guiding chamber 9, and in the thermal desorption room 17 the sample is extracted through a semi-permeable membrane 15 disposed in the thermal desorption room 17. As shown in FIG. 1, in the space within the outer chamber body 7, the inner gas guiding cylinder 5 is at the upper part, and outside the inner gas guiding cylinder 5 is the outer gas guiding chamber 9, the gas flows out of the inner gas guiding cylinder 5, and goes downwardly to the exhaust tube 27 at the bottom of the outer gas guiding chamber 9. In FIG. 1, the thermal desorption room 17 is below the inner gas guiding cylinder 5, and the gas passes around the thermal desorption room 17. In order to prevent impurities from entering the thermal desorption room 17, the thermal desorption room 17 is defined by the filtering screen 13. Sample or substance in the gas can enter the thermal desorption room 17. In the present embodiment, the semi-permeable membrane 15 defines a desorption space, and the sample in the outer gas guiding chamber 9 can pass through semi-permeable membrane 15 and enter the desorption space. The gathering and sampling device further includes a sample carrier gas tube 35 and a sample outlet 31, and a carrier gas is introduced from the sample carrier gas tube 35 and is mixed with the desorbed sample and then is discharged at the sample outlet 31. The semi-permeable membrane is configured to be supported by a support screen, to form a cylindrical structure of multiple-layered semi-permeable membranes or the grid structure of a multiple-layered semi-permeable membrane, so as to facilitate the gas to be mixed with the sample to contact the semi-permeable membrane, increasing contact area of the semi-permeable membrane with the sample. In FIG. 1, it is shown that the semi-permeable membrane supported by the support screen 16 has a cylindrical shape. In another embodiment, the support screen 16 is a multiple-layered structure, and each layer of the support screen is provided with the semi-permeable membrane, thereby forming the grid structure of multiple-layered semi-permeable membranes. The gas mixed with the sample passes through the multiple-layered semi-permeable membrane, increasing contact area of the semi-permeable membrane with the sample. The semi-permeable membrane 15 is a porous membrane, which can prevent water molecules, ammonia molecules and other impurities in the sample from passing through, and thus protects back-end analytical components and limits formation of clusters of molecules, thereby improving the resolution. In the embodiment shown in FIG. 1, a design of circular semi-permeable membrane 15 is adopted, which increases contact area of the semi-permeable membrane 15 with the sample, thereby achieving effective enrichment of sample molecules and reducing design requirements of sensitivity of back-end instrument.

An exhaust tube 27 is provided at a lower part of the side wall of the gas charging chamber 8, and the gas in the outer gas guiding chamber 9 is discharged through the exhaust tube 27 and is re-sent by air pump 29 to the gas charging chamber 8 for recycling. According to the embodiments of the disclosed technology, the gas discharged from the outer gas guiding chamber 9 can be recycled, which not only increases utilization efficiency of heated gas and reduces energy consumption, but also improves detection precision of the sample, because some of the sample can be desorbed and collected circularly. Moreover, this recycling can reduce pollution of the sample to the environment.

In the present embodiment, the outer chamber body 7 is surrounded by a thermal insulation layer 20, and a heater is provided in the outer chamber body 7 for controlling the outer chamber body 7 to be at a desired temperature.

It should be noted that, some known trace substance collecting and sampling devices are unable to efficiently collect high-boiling sample attached to an objected to be inspected, so they fail to inspect high-boiling substances. Since the outer chamber body 7 has higher temperature or predetermined temperature, the gas passed through the gas charging chamber 8 of the outer chamber body 7 is heated, and the cyclone and the gas injected by the plurality of gas injection orifices 36 are heated gas flow, which helps to blow off the high-boiling substances. In the embodiments of the disclosed technology, heated gas flow is adopted to impart the object to be inspected so that the particle samples on the objected are knocked down. Accordingly, the disclosed technology is a high efficient sampling device having wider selectivity on boiling points ranges of substances, which is especially suitable for safety inspection of drugs and explosives having high-boiling properties.

The gathering and sampling device shown in FIG. 1 will be described systemically hereinafter, however, it should be noted that embodiments of the disclosed technology is not limited to the configuration shown in FIG. 1, and for those skilled in the art, other configurations can be obtained by modifying or changing the configuration shown in FIG. 1.

As shown in FIG. 1, a gathering and sampling device, for example for trace substances, may, but not exclusively, include the following functional parts.

A jet impacting part includes a plurality of gas injection orifices 36 provided in a circumference of a trumpet-shaped inner housing 2 and a gas charging chamber 8 provided on the outer chamber body 7.

A cyclone generating part includes a gas charging tube 25, rotational flow tubes 26 and a gas charging chamber 8 provided in the outer chamber body 7, which makes the charged gas flow into a whirling; and a cyclone chamber 3 formed between the outer housing 1 and the trumpet-shaped inner housing 2 and a gas inlet 32 formed in the outer housing 1, which amplifies the whirling into a cyclone.

A sample absorbing part includes a sampling opening 44 at a center of the cyclone and for absorption of the sample; a flow guiding part includes an inner gas guiding chamber 6 formed between the trumpet-shaped inner housing 2 and the inner gas guiding cylinder 5, and an outer gas guiding chamber 9 formed between the hollow outer chamber body 7 and a bottom cover 10, which disperses particle sample into single molecules.

A desorption part includes a thermal desorption room 17 and a semi-permeable membrane 15 which are provided in the outer gas guiding chamber 9, and a sample inlet tube 30 and a sample carrier tube 35 provided at bottom of the thermal desorption room 17, which enriches and desorbs the dispersed sample molecules and then sends them to a downstream detector.

A temperature controlling part is consisted of a heating rod 18, a temperature sensor 19 and a thermal insulating sleeve 20.

The trumpet-shaped inner housing 2 seats on upper circumference portion of the outer chamber body 7 and is sealed by O-ring 22. The gas injection orifices 36 are provided at the circumference of the trumpet-shaped inner housing 2, and the gas injection orifices 36 is communicated with the gas charging chamber 8. The bottom cover 10 seals a lower opening of the outer chamber body 7 with O-ring 23. A tapered end of the trumpet-shaped inner housing 2 is sleeved in the inner gas guiding cylinder 5 to form the inner gas guiding chamber 6. Top cover 11 of the desorption room 17 is sleeved at lower end of a gas guiding cylinder 5 and is sealed by the O-ring 22. Bottom cover 14 of the desorption room 17 passes through the bottom cover 10 and is sealed by O-ring 24.

Figure 2:
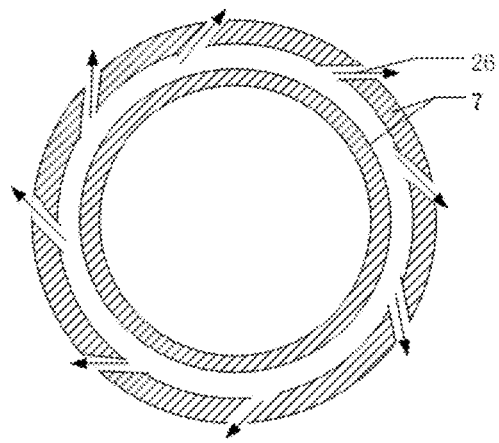
FIG. 2 is a schematic view of a cross section of a circumference at an upper part of an outer chamber body where a plurality of rotational flow tubes are provided, according to the embodiment of the disclosed technology.

Lower circumference portion of the outer housing 1 is sleeved on upper outer circumference portion of the outer chamber body 7. Gas charging tube 25 is provided at a middle of side wall of the gas charging chamber 8. A plurality of rotational flow tubes 26 are provided uniformly at upper circumference of the side wall of the gas charging chamber 8. As shown in FIG. 2, axes of the rotational flow tubes 26 are tangent with side wall of the outer chamber body 7, and angles of the axes of the rotational flow tubes 26 relative to a vertical direction are between 45°~90°, which helps formation of a cyclone from the passing gas flow. An exhaust tube 27 is provided at a lower part of the side wall of the gas charging chamber 8, and by air pump 29 the gas charging chamber 8 is charged through gas charging tube 25. In the gas charging chamber 8, a rather great gas flow is discharged from the rotational flow tubes 26 to form a whirling, the whirling rotates in the cyclone chamber 3 and causes external gas flow to be brought into the cyclone chamber 3 through gas inlet 32, thereby amplifying and forming a cyclone, another smaller gas flow is injected to a target 33 to be inspected through the gas injection orifices 36, and by strong impacting force of the heated gas flow, particle sample attached to surface of the target 33 to be inspected is hit down. Under the action of the adsorption force of negative pressure center of the tornado cyclone and the suction force of the downstream air pump 29, the particle sample hit down is adsorbed into the sampling opening 44 and then enters the inner gas guiding chamber 6.

With the heating unit 18, the temperature sensor 19 and the thermal insulating sleeve 20 provided on the outer chamber body 7, temperature in the chamber can be controlled. The inner gas guiding cylinder 5 is set to be at certain high temperature, such that the particles sample adsorbed are sufficiently dispersed into single molecules when passing through the inner gas guiding chamber 6, then enter the outer gas guiding chamber 9, and in the outer gas guiding chamber 9, the sample molecules enter the desorption room 17 through screen-shaped desorption cylinder, while non-gasified impurities are prevented from entering the desorption room 17 by the filtering screen 13.

In the desorption room 17 a circular semi-permeable membrane 15 is provided, and the semi-permeable membrane 15 is supported by a support screen 16. The semi-permeable membrane 15 can prevent impurities including water molecules, ammonia molecules and the like from entering analytical apparatus, and limit formation of cluster molecules, improving resolution of the apparatus. Sample molecules entering the desorption room 17 are enriched on the semi-permeable membrane 15, and permeate through the semi-permeable membrane 15 in high temperature. Air pump 34 pumps air into filter 28, and the filtered air enters the thermal desorption room 17 after passing through the sample carrier tube 35. Being carried by the sample carrier gas, sample molecules which have permeated through the semi-permeable membrane 15 enter downstream detector through the sample inlet tube 30. Meanwhile, the gas flow coming from the sampling opening 44 is discharged through the exhaust tube 27, and enters air pump 29 via tee joint 37. Under the action of the air pump 29, it enters the gas charging tube 25 again, for recycling. In addition, external clean air is pumped by the air pump 29 into the gas charging tube 25 through another passage of the tee joint 37, for supplying amount of wind required to form a cyclone. The disclosed technology achieves a fast and efficient collecting and sampling device having wider selectivity on boiling points ranges and enrichment property.

Some embodiments of the generally inventive concept have been illustrated and described, however, it should be understood by those skilled in the art that, changes on these embodiments can be made without departing from the principles and spirit of the generally inventive concept, and the scope of which is defined in the claims and their equivalents.

What is claimed is:

1. A gathering and sampling device, comprising:
a cylindrically outer housing comprising a first outer housing end opening;
an outer chamber body, wherein a circumference portion of the cylindrically outer housing is sleeved on an upper outer circumference portion of a first end of the outer chamber body, and wherein the circumference portion is opposite to the first outer housing end opening;
wherein the outer chamber body comprises: an inner housing formed by the upper outer circumference portion of the first end of the outer chamber body, the inner housing being disposed within the cylindrically outer housing and comprising a first inner housing end opening, a cyclone chamber being formed between the cylindrically outer housing and the inner housing to generate a cyclone by forming a gas flow within the cyclone chamber, and a plurality of gas injection orifices formed in the first inner housing end opening of the inner housing and configured to inject a gas from the outer chamber body outwards and towards a substantial center of a circular region defined by an end face of the first outer housing end opening of the cylindrically outer housing.

2. The gathering and sampling device of claim 1, wherein, the outer chamber body further comprises: a gas guiding chamber formed by inner space of the outer chamber body, and a sampling opening located at a center of the inner housing and configured to guide a gas sample, that is adsorbed to the gathering and sampling device through a center of the cyclone, into the gas guiding chamber.

3. The gathering and sampling device of claim 2, wherein, the outer chamber body further comprises a gas charging chamber formed in a side wall of the outer chamber body around the gas guiding chamber and a plurality of rotational flow tubes connected with the gas charging chamber and injecting the gas from the gas charging chamber into the cyclone chamber so as to generate the cyclone by injecting the gas flow into the cyclone chamber.

4. The gathering and sampling device of claim 3, wherein, the plurality of gas injection orifices are communicated with the gas charging chamber, and a gas-flow rate from the plurality of gas injection orifices is smaller than that from the plurality of rotational flow tubes.

5. The gathering and sampling device of claim 3, wherein, the plurality of rotational flow tubes are provided uniformly in a circumferential wall of the outer chamber body closing to the first inner housing end opening, and axes of the rotational flow tubes are tangent with side wall of the outer chamber body, and angles of the axes of the rotational flow tubes relative to a vertical direction are between 45°~90°.

6. The gathering and sampling device of claim 5, wherein, the outer housing is formed with at least one gas inlet, located at a lower part of the side wall of the outer housing, and at an opposite side of the first outer housing end opening relative to the rotational flow tubes, such that the gas is absorbed through the at least one gas inlet under the action of the cyclone generated in the cyclone chamber.

7. The gathering and sampling device of claim 2, wherein, the gas guiding chamber is provided therein with an inner gas guiding cylinder defining an inner gas guiding chamber, a gas guided in from the sampling opening enters about a bottom of the inner gas guiding chamber and then flows out of the inner gas guiding chamber through an inner gas guiding chamber opening.

8. The gathering and sampling device of claim 7, wherein, the inner gas guiding cylinder is configured to heat so as to increase a temperature of the gas entering the inner gas guiding cylinder.

9. The gathering and sampling device of claim 7, wherein, an outer wall of the inner gas guiding cylinder and an inner wall of the gas guiding chamber define an outer gas guiding chamber, a thermal desorption room defined by a filtering screen is formed within the outer gas guiding chamber, and in the thermal desorption room the sample is extracted through a semi-permeable membrane disposed in the thermal desorption room.

10. The gathering and sampling device of claim 9, wherein, the semi-permeable membrane defines a desorption space, the sample in the outer gas guiding chamber can pass through the semi-permeable membrane and enter the desorption space, and the gathering and sampling device further comprises a carrier gas tube and a sample outlet, and a carrier gas is introduced by the sample carrier tube and is mixed with the desorbed sample and then is discharged at the sample outlet;

wherein, the semi-permeable membrane is configured to be supported by a support screen, to form the cylindrical structure of multiple-layered semi-permeable membranes or the grid structure of a multiple-layered semi-permeable membrane, so as to facilitate the gas mixed with the sample to contact the semi-permeable membrane.

11. The gathering and sampling device of claim 9, wherein, an exhaust tube is provided at a lower part of the side wall of the gas charging chamber, and the gas in the outer gas guiding chamber is discharged through the exhaust tube and is re-sent by a pump to the gas charging chamber for recycling.

12. The gathering and sampling device of claim 1, wherein, an inner wall of the outer housing has a trumpet shape.

13. The gathering and sampling device of claim 1, wherein, the outer chamber body is surrounded by a thermal insulation layer, and a heater is provided in the outer chamber body for controlling the outer chamber body to be in a desired temperature.

14. An inspection apparatus comprising a gathering and sampling device, wherein the gathering and sampling device comprises:

a cylindrically outer housing comprising a first outer housing end opening;

an outer chamber body, wherein a circumference portion of the cylindrically outer housing is sleeved on an upper outer circumference portion of a first end of the outer chamber body, and wherein the circumference portion is opposite to the first outer housing end opening;

wherein the outer chamber body comprises: an inner housing formed by the upper outer circumference portion of the first end of the outer chamber body, the inner housing being disposed within the cylindrically outer housing and comprising a first inner housing end opening, a cyclone chamber being formed between the cylindrically outer housing and the inner housing to generate a cyclone by forming a gas flow within the cyclone chamber, and a plurality of gas injection orifices formed in the first inner housing end opening of the inner housing and configured to inject a gas from the outer chamber body outwards and towards a substantial center of a circular region defined by an end face of the first outer housing end opening of the cylindrically outer housing.

* * * * *